(12) United States Patent
Marcuccio et al.

(10) Patent No.: US 6,288,259 B1
(45) Date of Patent: Sep. 11, 2001

(54) ALKENE BORATES AND A PROCESS FOR COVALENTLY COUPLING ORGANIC COMPOUNDS

(75) Inventors: Sebastian Mario Marcuccio, Endeavour Hills; Mary Rodopoulos, Burwood East; Helmut Weigold, Mount Waverley, all of (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 0 days.

(21) Appl. No.: 09/445,457
(22) PCT Filed: Jun. 19, 1998
(86) PCT No.: PCT/AU98/00476
§ 371 Date: Mar. 6, 2000
§ 102(e) Date: Mar. 6, 2000
(87) PCT Pub. No.: WO98/58935
PCT Pub. Date: Dec. 30, 1998

(30) Foreign Application Priority Data

Jun. 20, 1997 (AU) .................................................. PO 7480

(51) Int. Cl.[7] .................................. C07F 5/04; C07F 5/02
(52) U.S. Cl. .................................................. 558/288; 562/7
(58) Field of Search ................................ 562/7; 558/288, 558/286

(56) References Cited

U.S. PATENT DOCUMENTS 2,402,591 * 6/1946 Laxler et al. .
3,219,682 * 11/1965 Woods et al. .
3,234,259 * 2/1966 Woods et al. .
3,553,170 * 1/1971 Woods et al. .

OTHER PUBLICATIONS

CA:656:2608 abs of Bull Soc Chim Fr by Braun et al (8) pp 2557–64, 1966.*
CA:83:28318 abs of Mikhailov in Pure Appl Chem 39(4) pp 505–23, 1974.*
CA:100:156674 abs of Oranometallics by Matteson et al. 3(4) pp 614–18, 1984.*
CA:115:208051 abs of Synthesis by Fontani et al (8) pp 605–9, 1991.*
Chemistry Letters (1996), "A Synthesis of (E)–(1–Organo–1–alkenyl) boronates by the Palladium–Catalyzed Cross–Coupling Reaction of (E)–1,2–Bis (boryl)–1–alkenes with Organic Halides: A Formal Carboration of Alkynes via the Diboration–Coupling Sequence", (T. Ishiyama, M. Yamamoto, N. Miyaura).
Macromolecules, (1996), "Conjugated Polymers with Main Chain Chirality. 1. Synthesis of an Optically Active Poly(A-sylenevinylene)", (Qiau–Sheng Hu et al.).
Tetrahedron Letters, 37:38, 1996, "A Synthesis of Allylboronates via the Palladium (O)—Catalyzed Cross–Coupling Reaction of Bis(pinacolato) diboron with allylic Acetates", (T. Ishiyama, T. Ahiko, N. Miyaura).

* cited by examiner

Primary Examiner—Jean F. Vollano
(74) Attorney, Agent, or Firm—Bacon & Thomas

(57) ABSTRACT

This invention describes a process for covalently coupling organic compounds which comprises reacting an olefinic compound having a halogen or halogen-like substituent at a coupling position with a diboron derivative in the presence of a Group VIII metal catalyst and a suitable base. The invention also describes a process for preparing alkene borate intermediates comprising reacting an olefinic compound having a halogen or halogen-like substituent with a diboron derivative in the presence of a Group VIII metal catalyst and a suitable base.

11 Claims, No Drawings

ALKENE BORATES AND A PROCESS FOR COVALENTLY COUPLING ORGANIC COMPOUNDS

This application is a 371 of PCT/AU98/00476 filed Jun. 19, 1998, now WO 98/58983.

This invention relates to a process for covalently coupling organic compounds, in particular to a process for covalently linking an olefinic moiety via an organoboron intermediate to other organic compounds. The invention also relates to a process for the preparation of the organoboron intermediates.

Process for forming covalent bonds between olefinic compounds and organic compounds, both inter- and intra-molecular, are of particular importance to the synthetic organic chemist. Many such reactions are known, each requiring its own special reaction conditions, solvents, catalysts, activating groups etc. Some known types of coupling reactions involving olefinic moieties include the Michael reaction and reactions described in the following references: Transition Metals in the Synthesis of Complex Organic Molecules (L. S. Hegedus, University Science Books, 1994, ISBN 0-935702-28-8); Handbook of Palladium Catalysed Organic Reactions (J. Malleron, J. Fiaud and J. Legros, Academic Press, 1997, ISBN 0-12-466615-9); Palladium Reagents and Catalysts (Innovations in Organic Synthesis by J. Tsuji, John Wiley & Sons, 1995, ISBN 0-471-95483-7); and N. Miyuara and A. Suzuki, Chem Rev. 1995, 95, 2457–2483.

Catalysts of palladium, its complexes and its salts are well recognised for activation of C—H bonds towards coupling reactions. In this regard the Heck reaction of an alkene with an aryl or vinyl halide in the presence of palladium derivatives has been the subject of intensive study. However commercial development of the Heck reaction has not progressed as rapidly as could have been expected. Other Group VIII metal catalysts, such as platinum, have also been used to activate such carbon bonds.

The success of the Heck reaction depends to a large extent on the substrates and the reaction conditions. When two β-hydrogens are present in the alkene the reaction generally leads to the formation of the (E)-alkenes which are often contaminated with the corresponding (Z)-alkenes.

Although alkene borates (alkenylborates) can be reacted with a variety of organic molecules to give coupled products via the formation of new carbon-carbon bonds (See for example the references above) the process for the preparation of the alkenylborates by the commonly used hydroboration reaction of alkynes is limited because of the difficulties that are encountered through the lack of regiochemisty and/or chemoselectivity (such as the reduction of a number of different functional groups) (See N. Miyuara and A. Suzuki, Chem Rev. 1995, 95, 2457–2483).

Improved methodologies are thus required for the synthesis of alkene borates.

It has now been found that alkene borates can be synthesised from haloalkenes or pseudo-haloalkenes under mild conditions and in the presence of a range of substituents. This process overcomes or at least alleviates one or more of the limitations encountered in the use of the hydroboration methodology and is fundamentally different in that the starting material is an alkene and not an alkyne. Coupling of the alkenylborates with an organic compound may be achieved in the presence of Group VIII metal catalyst and a suitable base.

Accordingly the invention provides a process for covalently coupling organic compounds which comprises reacting an olefinic compound having a halogen or halogen-like substituent in a vinylic coupling position with a diboron derivative in the presence of a Group VIII metal catalyst and a suitable base.

In one embodiment this process may be used to prepare a symmetrical product. In this embodiment the coupling proceeds in two steps. In the first step the diboron derivative reacts with an olefinic compound in the presence of the Group VIII metal catalyst and suitable base to form an alkene borate intermediate, this intermediate reacts in the presence of base with remaining olefinic compound. According to this embodiment the covalent coupling comprises a covalent bond between coupling positions of two molecules of olefinic compound.

Preferably the suitable base used to catalyse the reaction with the diboron derivative is also able to catalyse the coupling of the alkene borate intermediate to the remaining olefinic compound. However, if necessary, a stronger base can be added or the reaction mixture can be heated after the formation of the alkene borate intermediate to catalyse or promote the coupling reaction.

The process according to the invention also allows the preparation of unsymmetrical products. Accordingly in another embodiment of the invention there is provided a process for covalently coupling organic compounds which comprises:

reacting an olefinic compound having a halogen or halogen-like substituent at a vinylic coupling position with a diboron derivative in the presence of a Group VIII catalyst and a suitable base to form an alkene borate intermediate, and reacting the alkene borate intermediate with an organic compound having a halogen or halogen-like substituent at a coupling position in the presence of a Group VIII metal catalyst and a suitable base, whereby the olefinic compound is coupled to the organic compound via a direct bond between the respective coupling positions.

The process according to this embodiment allows the preparation of unsymmetrical compounds when the organic compound is different from the olefinic compound, although symmetrical products will be obtained if the organic compound is the same as the olefinic compound.

It is especially convenient to conduct the process in a single pot without isolation of the alkene borate intermediate, however it has been found that the presence of unreacted diboron derivative can interfere with the coupling step, resulting in the formation of unwanted by-products.

Accordingly in another embodiment of the present invention there is provided a process for covalently coupling organic compounds which comprises:

reacting an olefinic compound having a halogen or halogen-like substituent at a vinylic coupling position with a diboron derivative in the presence of a Group VIII metal catalyst and a suitable base to form an alkene borate intermediate, adding water or water and a suitable base to decompose excess diboron derivative, reacting the alkene borate intermediate with an organic compound having a halogen or halogen-like substituent at a coupling position in the presence of a Group VIII metal catalyst and a suitable base, whereby the olefinic compound is coupled to the organic compound via a direct bond between respective coupling positions.

Preferably the reaction is conducted in a single pot, although it is possible to isolate the alkene borate intermediate prior to the final coupling step. If the reaction is conducted in a single pot it is preferred that the base added to decompose the diboron derivative is suitable for catalysing the coupling reaction. In this case there is no need to add further base with the organic compound in the coupling reaction.

In another embodiment, after formation of the alkene borate intermediate, the coupling of the alkene borate intermediate with the organic compound is achieved by increasing the temperature of the reaction mixture to a temperature sufficient for said coupling reacting to occur. In this embodiment it may not be necessary to add a stronger base to catalyse the coupling reaction.

In cases where there is a need to remove excess diboron derivative but the use of water or water and base is deleterious because of the sensitivity of substituents, etc, or other factors the excess diboron derivative may be decomposed by addition of mild oxidising agents following the formation of the alkene borate intermediate.

Accordingly in a further embodiment there is provided a process for covalently coupling organic compounds which comprises:
  reacting an olefinic compound having a halogen or halogen-like substituent at a vinylic coupling position with a diboron derivative in the presence of a Group VIII metal catalyst and a suitable base to form an alkene borate intermediate;
  adding a mild oxidising agent to decompose excess diboron derivative;
  reacting the alkene borate intermediate with an organic compound having a halogen or halogen-like substituent at a coupling position in the presence of a Group VIII metal catalyst and a suitable base whereby the olefinic compound is coupled to the organic compound via a direct bond between respective coupling positions.

The mild oxidising agent may be any compound which will break the B—B bond of the diboron derivative but which is not strong enough to break boron-carbon bonds of the alkene borate intermediate. Suitable mild oxidising agents are N-chlorosuccinimide, dioxygen gas, chloramine-T, chloramine-B, 1-chlorotriazole, 1,3-dichloro-5,5-dimethylhydantoin, trichloroisocyanuric acid and dichloroisocyanuric acid potassium salt.

Oxidants such as hydrogen peroxide, ozone, bromine, t-butyl hydroperoxide, potassium persulphate, sodium hypochlorite and peracids, are too strong for use in this process; use of strong oxidants does not form part of this invention.

The terms "olefinic" and "olefinic compound" as used herein refer to any organic compound having at least one carbon to carbon double bond which is not part of an aromatic or pseudo aromatic system. The olefinic compounds may be selected from optionally substituted straight chain, branched or cyclic alkenes; and molecules, monomers and macromolecules such as polymers and dendrimers, which include at least one carbon to carbon double bond. Examples of suitable olefinic compounds include but are not limited to ethylene, propylene, but-1-ene, but-2-ene, pent-1-ene, pent-2-ene, cyclopentene, 1-methylpent-2-ene, hex-1-ene, hex-2-ene, hex-3-ene, cyclohexene, hept-1-ene, hept-2-ene, hept-3-ene, oct-1-ene, oct-2-ene, cyclooctene, non-1-ene, non-4-ene, dec-1-ene, dec-3-ene, buta-1,3-diene, penta-1,4-diene, cyclopenta-1,4-diene, hex-1,diene, cyclohexa-1,3-diene, cyclohexa-1,4-diene, cyclohepta-1,3,5-triene and cycloocta-1,3,5,7-tetraene, each of which may be optionally substituted. Preferably the straight chain branched or cyclic alkene contains between 2 and 20 carbon atoms.

In one embodiment the olefinic compound is a compound of formula I

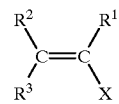

where $R^1$, $R^2$ and $R^3$ are each independently selected from alkyl, alkenyl, alkynyl, aryl, heteroaryl, acyl, arylalkyl and heteroarylalkyl (each of which may be optionally substituted), cyano, isocyano, formyl, carboxyl, nitro, halo, alkoxy, alkenoxy, aryloxy, benzyloxy, haloalkoxy, haloalkenyloxy, haloaryloxy, nitroalkyl, nitroalkenyl, nitroalkynyl, arylamino, diarylamino, dibenzylamino, alkenylacyl, alkynylacyl, arylacyl, acylamino, diacylamino, acyloxy, alkylsulphonyloxy, arylsulphenyloxy, heterocycloxy, arylsulphenyl, carboalkoxy, carboaryloxy, alkylthio, benzylthio, acylthio, sulphonamide, sulfanyl, sulfo, carboxy (including carboxylato), carbamoyl, carboximidyl, sulfinyl, sulfinimidyl, sulfinohydroximyl, sulfonimidyl, sulfondiimidyl, sulfonohydroximyl, sulfamyl, phosphorous containing groups (including phosphinyl, phosphinimidyl, phosphonyl, dihydroxyphosphanyl, hydroxyphosphanyl, phosphone (including phosphonato) and hydrohydroxyphosphoryl), guanidinyl, duanidino, ureido and ureylene, and X is a halogen or halogen-like substituent.

As used herein the term "organic compound having a halogen or halogen-like substituent at a coupling position" refers to any organic compound having a carbon to halogen or carbon to halogen-like substituent bond at a position where coupling to the olefinic compound is desired. The organic compound may be aliphatic, olefinic, allylic, acetylenic, aromatic, polymeric or dendritic. The compound may be an olefinic compound as defined above or part of such an olefinic compound. The organic compound may have one or more, preferably between 1 and 6, halogen or halogen-like substituents at coupling positions.

The terms "aromatic" and "aromatic compound(s)" as used herein refers to any compound or moiety which includes or consists of one or more aromatic or pseudoaromatic rings. The rings may be carbocyclic or heterocyclic, and may be mono or polycyclic ring systems. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoilne, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted. The terms "aromatic" and "aromatic compound(s)" includes molecules, and macromolecules, such as polymers, copolymers and dendrimers which include or consist of one or more aromatic or pseudoaromatic rings. The term "pseudoaromatic" refers to a ring system which is not strictly aromatic, but which is stablized by means of delocalization of π electrons and behaves in a similar manner to aromatic rings. Examples of pseudoaromatic rings include but are not limited to furan, thiophene, pyrrole and the like.

The term "coupling position" as used herein refers to a position on an organic compound at which coupling to another organic compound is desired. A coupling position on a carbon atom which is part of an olefinic carbon to carbon bond is also referred to as a "vinylic coupling position". Each olefinic compound or organic compound may have one or more, preferably between 1 and 6, coupling positions.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, isocyano, cyano, formyl, carboxyl, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxy silyl and arylphenoxy silyl.

The olefinic compound must include at least one halogen or halogen-like substituent at a vinylic coupling position to enable reaction with the diboron derivative. Similarly the organic compound must have at least one halogen or halogen-like substituent at a coupling position to enable reaction with the alkene borate intermediate. Preferred halogen substituents include I, Br and Cl. The reactivity of chloro substituted aromatic ring compounds can be increased by selection of appropriate ligands on the Group VIII metal catalyst. The terms "halogen-like substituent" and "pseudo-halide" refer to any substituent which, if present, may undergo substitution with a diboron derivative in the presence of a Group VIII metal catalyst and base to give an alkene borate intermediate, or if present on an organic compound may undergo substitution with an alkene borate intermediate to give a coupled product. Examples of halogen-like substituents include triflates and mesylates, diazonium salts, phosphates and those described in Palladium Reagents & Catalysts (Innovations in Organic Synthesis by J. Tsuji, John Wiley & Sons, 1995, ISBN 0-471-95483-7).

The process according to the present invention is especially suitable for coupling olefinic compounds containing substituents which are reactive with organometallic compounds, such as Grignard reagents or alkyl lithiums, therefore unsuitable for reacting using standard Grignard methodology unless these substituents are first protected. One such class of reactive substituents are the active hydrogen containing substituents. The term "active hydrogen containing substituent" as used herein refers to a substituent which contains a reactive hydrogen atom. Examples of such substituents include but are not limited to hydroxy, amino, imino, acetyleno, carboxy (including carboxylato), carbamoyl, carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene. Of these substituents it is particularly surprising that the reaction can be conducted with hydroxy and amino substituents in view of their high reactivity. Carboxyl, sulfo and the Rike (i.e. acidic) substituents may require additional base. Other reactive substituents include trimethylsilyl.

In the above definitions, the term "alkyl", used either alone or in compound words such as "alkenyloxyalkyl", "allkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecy, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alklynyl" denotes groups formed from straight chain, branched or cyclic alkyne including those structurally similar to the alkyl and cycloalkyl groups as previously defined, preferably $C_{2-20}$ alkynyl. Examples of alkynyl include ethynyl, 2-propynyl and 2- or 3-butynyl.

The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The terms "heterocyclic", "heterocyclyl" and "heterocycl" as used herein on their own or as part of a term such as "heterocyclicalkenoyl", "heterocycloxy" or "haloheterocyclyl" refer to aromatic, pseudo-aromatic and non-aromatic rings or ring systems which contain one or more heteroatoms selected from N, S, O and P and which may be optionally substituted. Preferably the rings or ring systems have 3 to 20 carbon atoms. The rings or ring systems may be selected from those described above in relation to the definition of "aromatic compound(s)".

The term "aryl" as used herein on its own or as part of a group such as "haloaryl" and "aryloxycarbonyl" refers to aromatic and pseudo-aromatic rings or ring systems composed of carbon atoms, optionally together with one or more heteroatoms. Preferably the rings or ring systems have between 3 and 20 carbon atoms. The rings or ring systems may be optionally substituted and may be selected from those described above in relation to the definition of "aromatic compound(s)".

The diboron derivative may be an ester or other stable derivative of diboronic acid. Examples of suitable esters include those of the formula (RO)$_2$B—B(RO)$_2$ where R is optionally substituted alkyl or optionally substituted aryl or —B(OR)$_2$ represents a cyclic group of formula

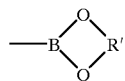

where R' is optionally substituted alkylene, arylene or other divalent group comprising linked aliphatic or aromatic moieties. Preferred diboron derivatives include bis(pinacolato)diboron (the pinacol ester of diboronic acid), bis(ethanediolato)diboron, bis(n-propanediolato)diboron and bis(neopentanediolato)diboron. Some of the diboron derivatives will be more readily amenable to subsequent hydrolysis than others and may allow for the use of milder reaction conditions. Furthermore, judicious choice of the diboron derivative used may facilitate control over the reaction products formed. The diboron ester derivatives may be made following the method of Brotherton et al. [R. J. Brotherton, A. L. McCloskey, L. L. Peterson and H. Steinberg, *J. Amer. Chem. Soc.* 82, 6242 (196); R. J. Brotherton, A. L. McCloskey, J. L. Boone and H. M. Manasevit, *J. Amer. Chem. Soc.* 82, 6245 (1960)]. In this process B(NMe$_2$)$_3$, obtained by reaction of BCl$_3$ with NHMe$_2$, is converted to BrB(NMe$_2$)$_2$ by reaction with a stoichiometric amount of BBr$_3$. Reduction in refluxing toluene with sodium metal gives the diboron compound [B(NMe$_2$)$_2$]$_2$ which, after purification by distillation, can be reacted with the alcohol (for example, pinacol) in the presence of a stoichiometric amount of HCl to give the desired ester product. Bis(neopentanediolato)diboron is described by Nguyen et al [Nguyen, P., Lesley, G., Taylor, N. J., Marder, T. B., Pickett, N/L/, Clegg, W., Elsegood, M. R. J., and Nonma, N. C., *Inorganic Chem.* 1994, 33, 4623–24]. Other methods for the preparation of the diboron derivatives would be known to those in the art.

The term "Group VIII metal catalyst" as used herein refers to a catalyst comprising a metal of Group 8 of the periodic table described in Chemical and Engineering News, 63(5), 27, 1985. Examples of such metals include Ni, Pt and Pd. Preferably the catalyst is a palladium catalyst as described below, although analogous catalysts of other Group VIII metals may also be used. Examples of suitable Ni catalysts include nickel black, Raney nickel, nickel on carbon and nickel clusters or a nickel complex. Examples of suitable Pt catalysts include platinum black, platinum on carbon and platinum clusters or a platinum complex. The Group VIII metal catalyst may additionally include other metals.

The palladium catalyst may be a palladium complex. Examples of suitable palladium catalysts include but are not limited to PdCl$_2$, Pd(OAc)$_2$, PdCl$_2$(dppf)CH$_2$Cl$_2$, Pd(PPh$_3$)$_4$ and related catalysts which are complexes of phosphine ligands, (such as (Ph$_2$P(CH$_2$)$_n$PPh$_2$) where n is 2 to 4, P(o-tolyl)$_3$, P(i-Pr)$_3$, P(cyclohexyl)$_3$, P(o-MeOPh)$_3$, P(p-MeOPh)$_3$, dppp, dppb, TDMPP, TTMPP, TMPP, TMSPP and related water soluble phosphines), related ligands (such as triarylarsine, triarylantimony, triarylbismuth), phosphite ligands (such as P(OEt)$_3$, P(O-p-tolyl)$_3$, P(O-o-tolyl)$_3$ and P(O-iPr)$_3$) and other suitable ligands including those containing P and/or N atoms for co-ordinating to the palladium atoms, (such as for example pyridine, alkyl and aryl substituted pyridines, 2,2'-bipyridyl, alkyl substituted 2, 2'-bipyridyl and bulky secondary or tertiary amines), and other simple palladium salts either in the presence or absence of ligands. The palladium catalysts include palladium and palladium complexes supported or tethered on solid supports, such as palladium on carbon, as well as palladium black, palladium clusters, palladium clusters containing other metals, and palladium in porous glass as described in J. Li, A. W-H. Mau and C. R. Strauss, Chemical Communications, 1997, p1275. The same or different palladium catalysts may be used to catalyse different steps in the process. The palladium catalyst may also be selected from those described in U.S. Pat. No. 5,686,608. In certain reactions there are advantages in using ligands with altered basicity and/or steric bulk.

The process may be performed in any suitable solvent or solvent mixture. Examples of such solvents include lower alcohols, and their esters with the lower aliphatic carboxylic acids, cyclic and the lower secondary and tertiary amines, amides of the lower aliphatic carboxylic acids and lower aliphatic secondary amines, DMSO, aromatic hydrocarbons, nitromethane, acetonitrile, benzonitrile, ethers, polyethers, cyclic ethers, lower aromatic ethers, and mixtures thereof, including mixtures with other solvents.

Preferred solvents include methanol, ethanol, isopropanol, DMSO, DMF, dioxane, DME, diethyl ether, THF or mixtures thereof with other solvents. Exclusion of water from the solvents is generally not essential and in some cases the presence of water is preferred. The addition of further diboron derivative may be useful when the solvents are not anhydrous.

The temperature at which each step of the process according to the invention is conducted will depend on a number of factors including the desired rate of reaction, solubility and reactivity of the reactants in the selected solvent, boiling point of the solvent, etc. The temperature of the reaction will generally be in the range of −100 to 250° C. In a preferred embodiment the process is performed at a temperature between 0 and 120° C., more preferably between 0 and 80° C., and most preferably between 15 and 40° C.

The term "suitable base" as used herein refers to a basic compound which, when present in the reaction mixture, is capable of catalysing, promoting or assisting reaction between reactants. The base may be suitable for catalysing a single step, or more than one step, depending on the desired outcome of the reaction. For example a base may be chosen which catalyses reaction between the olefinic compound and the diboron derivative, but which is not strong enough under the conditions used in the reaction to catalyse further reaction of the alkene borate intermediate with additional compound or other organic compound. In this case water or water and a stronger base may be added to decompose excess diboron derivative, and which may also catalyse reaction of the alkene borate intermediate with the organic compound. It is also preferable that a base is chosen which is soluble in the solvent to which it is added. Examples of bases which are suitable for catalysing the reaction of the olefinic compound with the diboron derivative include, aryl and alkyl carboxylates (for example potassium acetate), fluorides, hydroxides and carbonates of Li, Na, K, Rb, Cs, ammonium, alkylammonium, Mg, Ca, & Ba; phosphates and arylphosphates of Li, Na, K, Rb and Cs; phosphate esters (eg. $C_6H_5OP(O)(ONa)_2$) of Li, Na, K, Rb, Cs, ammonium and alkylammonium; phenoxides of Li, Na, K, Rb and Cs; alkoxides of Li, Na, K, Rb and Cs; and thallium hydroxide. Some of these bases may be used in conjunction with a phase transfer reagent, such as for example tetraalkylammonium salts or the crown ethers.

Examples of bases suitable for catalysing reaction of the olefinic compounds with the diboron derivative, without generally catalysing the further reaction of the alkene borate intermediate, include aryl and alkyl carboxylates, fluorides, and phosphates of Li, Na, K, Rb, Cs, ammonium and alkylammonium. Depending upon the reaction temperature stronger bases, such as carbonates, may be used.

Examples of bases suitable for decomposing excess diboron derivative and/or catalysing reaction of the alkene borate intermediate with the organic compound include the stronger bases listed above, including cesium carbonate, potassium carbonate, potassium phosphate and alkali metal hydroxides.

As used herein the term "alkene borate intermediate" refers to the product of the Group VIII metal base catalysed reaction between an olefinic compound having a halogen or halogen-like substituent at a vinylic coupling position and a diboron derivative, the product including a carbon- to -boron bond at the coupling position.

In another aspect of the invention there is provided a process for preparing an alkene borate intermediate comprising reacting a diboron derivative with an olefinic compound having a halogen or halogen-like substituent and an active hydrogen containing substituent in the presence of a Group VIII metal catalyst and a suitable base.

In a further aspect of the invention there is provided a process for preparing an alkene borate intermediate, comprising reacting a diboron derivative with an olefinic compound having a halogen or halogen-like substituent in a protic solvent in the presence of a Group VIII metal catalyst and a suitable base.

A first step in the purification of the alkene borate intermediate so formed may be the decomposition of any excess diboron derivative by the use of water, water and suitable base, or by the use of a mild oxidising agent.

In a further aspect of the invention there is provided a process for the preparation of an olefinic boronic acid by hydrolysing the alkene borate intermediate as hereinbefore described using established procedures. The ease of hydrolysis is a function of the diboronic ester used. Some alkene borate intermediates are more amenable to hydrolysis than those derived from bis(pinacolato)diboron. This method only relates to alkene borate intermediates which are boronic esters.

Some of the alkene borate intermediates and olefinic boronic acids are novel and represent a further aspect of the present invention. Examples of such novel alkene borate intermediates which may be prepared according to the present invention are listed in Table 2, while some known alkene borate intermediates prepared in accordance with the present invention are listed in Table 1.

TABLE 1

KNOWN ALKENE BORATES PREPARED BY DIBORON METHODOLOGY

| COMPOUND NUMBER | COMPOUND STRUCTURE | Calc M/Z | Found M/Z |
|---|---|---|---|
| 1 | (pinacol boronate of isobutenyl, with CH₃, CH₃ groups) | 182 | 183 (M⁺ + 1) |
| 2 | (pinacol boronate with –Si(CH₃)₃ substituent) | 240 | 241 (M⁺ + 1) |

TABLE 1-continued

KNOWN ALKENE BORATES PREPARED BY DIBORON METHODOLOGY

| COMPOUND NUMBER | COMPOUND STRUCTURE | Calc M/Z | Found M/Z |
|---|---|---|---|
| 3 | 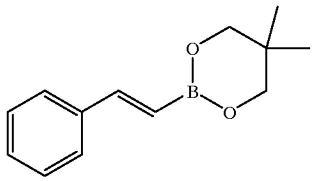 | 216 | 217 ($M^+ + 1$) |
| 4 | 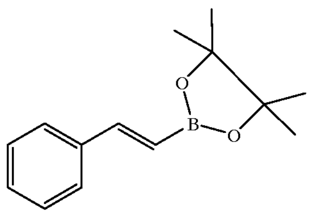 | 230 | 231 ($M^+ + 1$) |

TABLE 2

NOVEL ALKENE BORATES PREPARED BY DIBORON METHODOLOGY

| COMPOUND NUMBER | COMPOUND STRUCTURE | Calc M/Z | Found M/Z |
|---|---|---|---|
| 5 | | 196 | 197 ($M^+ + 1$) |
| 6 | | 182 | 183 ($M^+ + 1$) |
| 7 | | 368 | 369 ($M^+ + 1$) |
| 8 | 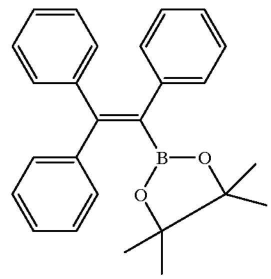 | 383 | 384 ($M^+ + 1$) |
| 9 | 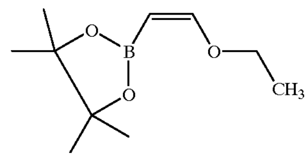 | 198 | 199 ($M^+ + 1$) |
| 10 | 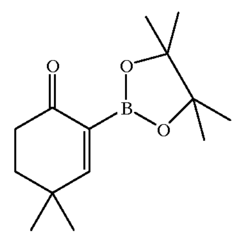 | 250 | 251 ($M^+ + 1$) |
| 11 | 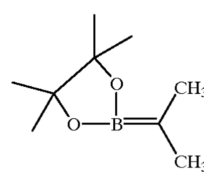 | 193 | 194 ($M^+ + 1$) |
| 12 | 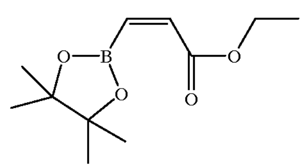 | 226 | 227 ($M^+ + 1$) |
| 13 | 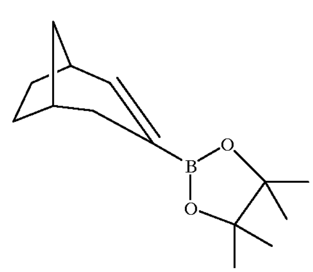 | 234 | 235 ($M^+ + 1$) |

TABLE 2-continued

NOVEL ALKENE BORATES PREPARED BY DIBORON METHODOLOGY

| 14 | [structure] | 300 | 257 (M⁺ + 1 − B(OH)₂) |

| COMPOUND | NAME |
|---|---|
| 5. | 2-(1,2-Dimethylprop-1-enyl)-4,4,5,5-tetramethyl-1,3,2-dioxaborolane. |
| 6. | 2-(1,2-Dimethylprop-1-enyl)-5,5-dimethyl-1,3,2-dioxaborinane. |
| 7. | 5,5-Dimethyl-2-(1,2,2-triphenylvinyl)-1,3,2-dioxaborinane. |
| 8. | 4,4,5,5-Tetramethyl-2-(1,2,2-triphenylvinyl)-1,3,2-dioxaborolane. |
| 9. | Ethyl (Z)-2(4,4,5,5-tetramethyl-1,3,2-dioxaborolan-2-yl)ethenyl ether. |
| 10. | 4,4-Dimethyl-2-(4,4,5,5-tetramethyl-1,3,2-dioxaborolan-2-yl)cyclo-hex-2-en-1-one. |
| 11. | (E)-2-Methyl-3(4,4,5,5-tetramethyl-1,3,2-dioxaborolan-2-yl)prop-2-enenitrile. |
| 12. | Ethyl (Z)-3-(4,4,5,5-tetramethyl-1,3,2-dioxaborolan-2-yl)prop-2-enoate. |
| 13. | 2-Bicyclo[3.2.1]oct-2-en-3yl-4,4,5,5-tetramethyl-1,3,2-dioxaborolane. |
| 14. | 1,2,2-Triphenylvinylboronic acid. |

The term "linking group" as used herein refers to any chain of atoms linking one aryl group to another. Examples of linking groups include polymer chains, optionally substituted alkylene group and any other suitable divalent group.

The process according to the present invention is applicable to chemistry on solid polymer support or resin bead in the same manner as conventional chemistry is used in combinatorial chemistry and in the preparation of chemical libraries. Thus a suitable organic compound having a halogen or halogen-like substituent at a coupling position which is chemically linked to a polymer surface may be reacted with an alkene borate intermediate in the presence of a Group VIII metal catalyst and a suitable base to form a coupled product linked to the surface of the polymer. Excess reagents and by-products may then be washed away from the surface leaving only the reaction product on the surface. The coupled product may then be isolated by appropriate cleavage of the chemical link from the polymer surface. The process is also possible using the alternative strategy of reacting an olefinic compound having a halogen or halogen-like substituent linked to a polymer surface with a diboron derivative in the presence of a Group VIII metal catalyst and a suitable base to form an alkene intermediate chemically linked to the polymer surface. This intermediate may then be reacted with an organic compound having a halogen or halogen-like substituent at a coupling position in the presence of a Group VIII metal catalyst and a suitable base to prepare the coupled product chemically linked to the polymer. Excess reactants and by-products may be removed by suitable washing and the coupled product may be isolated by chemically cleaving the link to the polymer.

It is also possible to prepare polymers by reaction of olefinic compounds having more than one halogen or halogen-like substituent in a vinylic coupling position. Such olefinic compounds may be reacted with a diboron derivative in the presence of a Group VIII metal catalyst and a suitable base to form an alkene borate intermediate having more than one boron functionality. These intermediates may be reacted with organic compounds having more than one halogen or halogen-like substituent to form a polymer. If the olefinic compound has three or more halogen or halogen-like substituents which react with the diboron derivative then it is possible to prepare dendritic molecules in accordance with the process of the present invention.

The olefinic compound and the organic compound may be separate molecules, or may be linked together such that the alkene borate intermediate formed after reaction with the diboron derivative is able to react at a coupling position located elsewhere in the molecule so as to provide for an intramolecular reaction, such as a ring closure reaction. Similarly the process according to the invention allows intramolecular linking to occur between double bonds located in different parts of a molecule, provided each double bond has a vinylic halogen or halogen-like substituent.

The process according to the invention is also useful for the preparation of reactive intermediates which, after coupling, take part in further reactions or rearrangements. An example of such an intermediate is one formed by reaction of an ether containing vinylic halide with one of R¹, R² or R³ (formula I) being —OR with a diboron derivative. The subsequent coupling of the resulting alkene borate intermediate with an organic compound gives a ketone on hydrolysis of the ether.

The process according to the present invention provides an alternative method for coupling olefinic moieties to organic compounds. The process allows the use of mild conditions and avoids the use of expensive, difficult to handle and/or toxic reagents and solvents. In this regard boron and boron compounds are generally non-toxic. The reactions may also be performed in relatively cheap solvents such as methanol and ethanol and, in view of the improved control over the reaction steps, it is envisaged that it would be possible to perform the reactions on an industrial scale. In view of the mild reaction conditions it is also possible to perform the coupling without the need to protect most reactive substituents.

The following examples are provided to illustrate preferred embodiments of the invention.

However it is to be understood that the following description is not to supersede the generality of the invention previously described.

EXAMPLES

Example 1

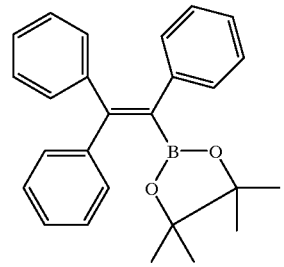

(a) Bis(pinacolato)diboron (0.283 g; 1.11 mmol), bromotriphenylethylene (0.337 g, 1.0 mmol), PdCl₂(dppf)

. CH₂Cl₂(26.4 mg), and (C₆H₅)P(O)(ONa)₂.H₂O (0.712 g; 3.01 mmol) were stirred in ethanol (5 ml) at 80° C. for 17 h. The gc of the reaction solution in ether, after washing with water, had one major peak (over 70% of total integral) identified as the desired alkene borate by retention time—gc/mass spectroscopy. The other peaks in the gc were identified as the starting materials and triphenylethylene. The reaction conditions (time/temperature) were not optimised.

(b) The product can also be made under the above reaction conditions with the phosphate base being replaced by CsF or K₂CO₃. With potassium acetate or Cs₂CO₃ as base, the reaction (80° C. in alcohol) gives higher amounts of triphenylethylene. DMSO can be used as reaction solvent and at 80° C./16.5 h gives the desired product together with triphenylethylene.

(c) The above reaction can be carried out successfully at lower temperatures with a strong base such as potassium carbonate. For example reaction of bis(pinacolato)diboron (0.142 g; 0.56 mmol), bromotriphenylethylene (0.168 g, 0.5 mmol), 12.8 mg PdCl₂(dppf).CH₂Cl₂ and K₂CO₃ (0.211 g ; 1.53 mmol) in ethanol (5 ml) at 30° C. gave, after 18 h reaction time, the triphenylethenylboronic acid ester together with a little triphenylethylene. The only other peak was due to a trace (less than 2% of area integrated) of unreacted bis(pinacolato)diboron.

Example 2

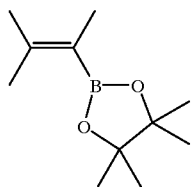

Bis(pinacolato)diboron (0.281 g; 1.11 mmol), K₂CO₃ (0.409 g; 2.96 mmol) and 50 mg of palladium (10%) on charcoal were placed in a reaction tube under nitrogen. After addition of 2-bromo-3-methyl-2-butene (0.152 g; 1.02 mmol) and dry ethanol (5 ml) the reaction was stirred at 30° C. for 19.5 h. The gc of the reaction solution, after washing an aliquot dissolved in ether with water, demonstrated the presence of the desired alkene borate.

Example 3

Bis(pinacolato)diboron (0.281 g; 1.11 mmol), K₂CO₃ (0.404 g; 2.93 mmol) and 27 mg of bis(benzonitrile) dichloropalladium were placed in a reaction tube under nitrogen. After addition of 2-bromo-3-methyl-2-butene (0.146 g; 0.98 mmol) and dry ethanol (5 ml) the reaction was stirred at 30° C. for 19.5 h. The gc of the reaction solution, after washing an aliquot dissolved in ether with water, demonstrated the presence of the desired alkene borate. This was confirmed by gc/ms.

The formation of this ester was also catalysed in ethanol by NiCl₂(dppf).CH₂Cl₂ and nickel acetate tetrahydrate at 30° C. using K₂CO₃ as base.

cis-Dichlorobis(diphenylphosphine)platinum and tetrakis(triphenylphosphine)platinum were also found to catalyse the formation of the pinacol alkenylborate from 2-bromo-3-methyl-2-butene and bis(pinacolato)diboron at 30° C. in methanol in the presence of K₂CO₃.

The dichloropalladium complex with 1,4-bis(diphenylphosphino)butane in ethanol at 30° C., catalysed the formation of the triphenylethylylboronic acid pinacol ester from bromotriphenylethylene and bis(pinacolato)diboron in the presence of K₂CO₃ as base.

Example 4

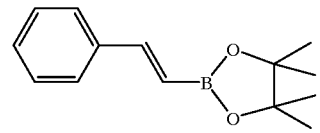

Bis(pinacolato)diboron (0.282 g; 1.11 mmol), 25 mg PdCl₂(dppf).CH₂Cl₂ and potassium acetate(0.300 g; 3 mmol) were placed in a reaction tube under nitrogen. After addition of β-bromostyrene (0.1 89 g; 1.03 mmol) and dry ethanol (5 ml) the reaction solution was stirred at 30° C. for 16 h. The gc of the reaction solution, after washing an aliquot dissolved in ether with water, had a peak identified by gc/ms as the product styrylboronic acid pinacol ester.

Example 5

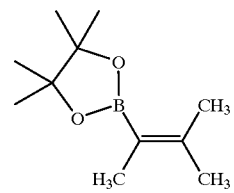

In a Schlenk tube under nitrogen, a mixture of bis(pinacolato)diboron (253 mg; 0.996 mmol), 2-bromo-3-methyl-2-butene (136 mg; 0.913 mmol), PdCl₂(dppf).CH₂Cl₂ (22 mg; 0.027 mmol) and potassium carbonate (380 mg; 2.75 mmol) in dry isopropyl alcohol (6 ml) was sealed and stirred at 30° C. for 18 h. Gas chromatographic analysis of the reaction mixture showed a major peak identified as the desired alkene borate by gc/ms as well as some unreacted diboron compound, and alkene halide starting material.

Example 6

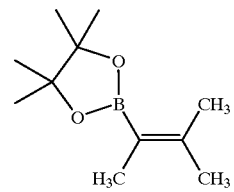

In a Schlenk tube under nitrogen, a mixture of bis(pinacolato)diboron (327 mg; 1.29 mmol), 2-bromo-3-methyl-2-butene (171 mg; 1.15 mmol), PdCl₂(dppf).CH₂Cl₂ (61 mg; 0.075 mmol) and potassium carbonate (475 mg; 3.44 mmol) in dry dioxane (5.5 ml) was sealed and stirred at 30° C. After 3 days, gc analysis of the reaction mixture showed three major peaks, identified as the desired alkene borate, and unreacted starting materials by gc/ms.

Example 7

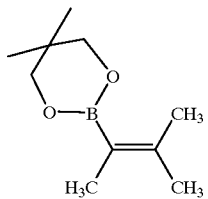

In a Schlenk tube under nitrogen, a mixture of bis(neopentanediolato)diboron (247 mg; 1.09 mmol), 2-bromo-3-methyl-2-butene (148 mg; 0.993 mmol), PdCl$_2$(dppf).CH$_2$Cl$_2$ (26 mg; 0.032 mmol) and potassium carbonate (426 mg; 3.08 mmol) in dry isopropyl alcohol (6 ml) was sealed and stirred at 30° C. After 16.5 h gc analysis of the reaction mixture showed two major peaks, identified as the desired alkene borate, and unreacted alkene halide by gc/ms. Only traces of diboron compound and dimer were detected.

Example 8

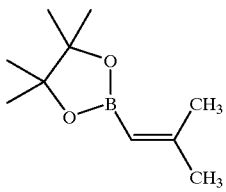

In a Schlenk tube under nitrogen, a mixture of bis(pinacolato)diboron (412 mg; 1.62 mmol), 2-bromo-2-methylpropene (197 mg; 1.46 mmol), PdCl$_2$(dppf).CH$_2$Cl$_2$ (40 mg; 0.049 mmol) and potassium acetate (440 mg; 4.48 mmol) in dry DMSO (8 ml) was sealed and stirred at 30° C. After 17 h gc analysis of the reaction mixture showed two major peaks, identified as the desired alkene borate and unreacted diboron compound by gc/ms.

Example 9

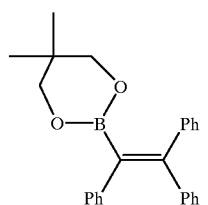

In a Schlenk tube under nitrogen, a mixture of bis(neopentanediolato)diboron (185 mg; 0.819 mmol), bromotriphenylethylene (253 mg; 0.755 mmol), PdCl$_2$(dppf).CH$_2$Cl$_2$ (21 mg; 0.026 mmol) and potassium acetate (237 mg; 2.41 mmol) in dry DMSO (5 ml) was sealed and stirred at 80° C. After 17 h gc analysis of the reaction mixture showed a major peak, identified as the alkene borate by gc/ms.

Example 10

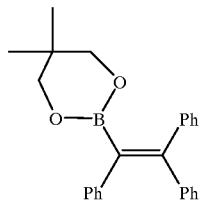

In a Schlenk tube under nitrogen, a mixture of bis(neopentanediolato)diboron (189 mg; 0.837 mmol), bromotriphenylethylene (255 mg; 0.761 mmol), PdCl$_2$(dppf).CH$_2$Cl$_2$ (24 mg; 0.029 mmol) and potassium acetate (251 mg; 2.56 mmol) in dry ethanol (5.5 ml) was sealed and stirred at 80° C. After 18 h, gc analysis of the reaction mixture showed three major peaks, identified as the desired alkene borate, alkene halide and the dehalogenated alkene by gc/ms.

Example 11

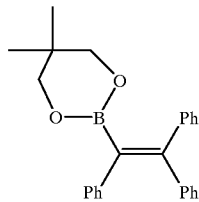

In a Schlenk tube under nitrogen, a mixture of bis(neopentanediolato)diboron (187 mg; 0.828 mmol), bromotriphenylethylene (251 mg; 0.749 mmol), PdCl$_2$(dppf).CH$_2$Cl$_2$ (20 mg; 0.024 mmol) and potassium carbonate (325 mg; 2.35 mmol) in dry ethanol (5.5 ml) was sealed and stirred at 80° C. After 18 h, gc analysis of the reaction mixture showed two major peaks, identified as the desired alkene borate and dehalogenated alkene by gc/ms.

Example 12

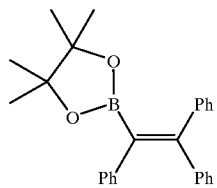

In a Schlenk tube under nitrogen, a mixture of bis(pinacolato)diboron (255 mg; 1.00 mmol), bromotriphenylethylene (298 mg; 0.889 mmol), PdCl$_2$(dppf).CH$_2$Cl$_2$ (26 mg; 0.032 mmol) and potassium carbonate (376 mg; 2.72 mmol) in dry isopropyl alcohol (5 ml) was sealed and stirred at 30° C. After 18 h gc analysis of the reaction mixture showed a major peak, identified as the desired alkene borate by gc/ms.

Example 13

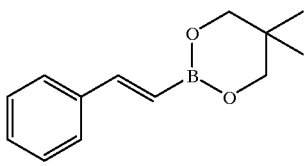

In a Schlenk tube under nitrogen, a mixture of bis(neopentanediolato)diboron (277 mg; 1.23 mmol), β-bromostyrene (202 mg; 1.10 mmol), PdCl$_2$(dppf).CH$_2$Cl$_2$ (29 mg; 0.036 mmol) and potassium acetate (329 mg; 3.35 mmol) in dry DMSO (5 ml) was sealed and stirred at 80° C. After 18 h, gc and gc/ms analyses detected alkene borate, dimer, and diboron compound.

Example 14

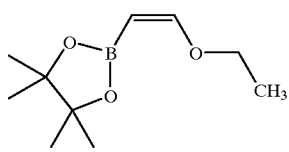

In a Schlenk tube under nitrogen, a miter of bis(pinacolato)diboron (284 mg; 1.12 mmol), cis-1-bromo-2-ethoxyethylene (152 mg; 1.01 mmol), PdCl$_2$(dppf).CH$_2$Cl$_2$ (53 mg; 0.065 mmol) and potassium carbonate (418 mg; 3.02 mmol) in dry methanol (5 ml) was sealed and stirred at 30° C. After 16 h gc and gc/ms analyses detected alkene halide, diboron compound, alkene borate and dimer.

Example 15

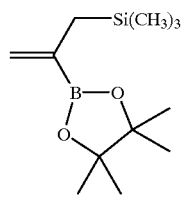

In a Schlenk tube under nitrogen, a mixture of bis(pinacolato)diboron (251 mg; 0.988 mmol), 2-bromoallyltrimethylsilane (172 mg; 0.890 mmol), PdCl$_2$(dppf).CH$_2$Cl$_2$ (45 mg; 0.055 mmol) and potassium carbonate (383 mg; 2.77 mmol) in dry methanol (5.5 ml) was sealed and stirred at 30° C. for 16.5 h. The gc of the reaction solution showed one major peak identified as the alkene borate by gc/ms.

Example 16

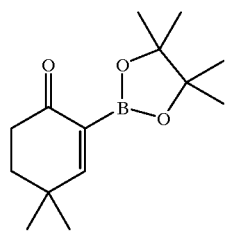

In a Schlenk tube under nitrogen, a mixture of bis(pinacolato)diboron (249 mg; 0.981 mmol), 4,4-dimethyl-2-iodo-2-cyclohexenone (220 mg; 0.880 mmol), PdCl$_2$(dppf).CH$_2$Cl$_2$ (44 mg; 0.054 mmol) and potassium carbonate (386 mg, 2.79 mmol) in dry methanol (5 ml) was sealed and stirred at 30° C. for 25.5 h. The gc of the reaction solution showed three major peaks identified as the alkene borate, alkene halide and diboron compound starting materials by gc/ms.

Example 17

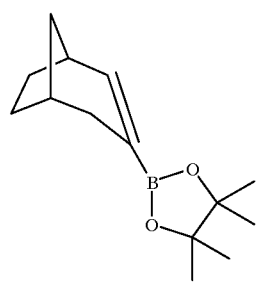

Bis(pinacolato)diboron (0.280 g; 1.10 mmol), 26 mg PdCl$_2$(dppf).CH$_2$Cl$_2$ and 0.419 g (3 mmol) K$_2$CO$_3$ were placed in a reaction tube under nitrogen. After addition of 0.140 g (0.98 mmol) 3-chlorobicyclo[3.2.1]oct-2-ene and 5 ml dry ethanol the reaction solution was stirred at 30° C. for 24 h. The gc of the reaction solution, after washing an aliquot dissolved in ether with water, had a peak identified by gc/ms (m/z=235; M$^+$+1) as the desired alkene borate. The product is also formed under the same reaction conditions using CsF (0.61 g, 4 mmol) as base instead of K$_2$CO$_3$.

Example 18

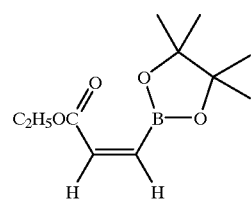

Bis(pinacolato)diboron (0.284 g; 1.12 mmol), 24 mg PdCl$_2$(dppf).CH$_2$Cl$_2$ and 0.413 g (3 mmol) K$_2$CO$_3$ were placed in a reaction tube under nitrogen. After addition of 0.232 g (1.03 mmol) ethyl cis-iodoacrylate and 5 ml dry ethanol the reaction solution was stirred at 25° C. The gc of the reaction solution, after washing an aliquot dissolved in ether with water, had a peak identified by gc/ms [m/z=227

($M^+$+1), m/z=255 ($M^+$+29), m/z=267 ($M^+$+41)] as the desired alkene borate. The product is also formed under the same reaction conditions using CsF (0.61 g, 4 mmol) as base instead of $K_2CO_3$.

Example 19

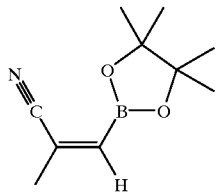

Bis(pinacolato)diboron (0.284 g; 1.12 mmol), 50 mg $PdCl_2$(dppf).$CH_2Cl_2$ and 0.61 g (4 mmol) CsF were placed in a reaction tube under nitrogen. After addition of 0.143 g (0.98 mmol) 2-bromo-2-methylacrylonitrile and 4 ml dry dioxane and 1 ml pyridine the reaction solution was stirred at 50° C. for 19 h. The gc/ms of the reaction solution, after washing an aliquot dissolved in ether with water, indicated that the desired alkene borate had formed [m/z=193 ($M^+$+1), m/z=222 ($M^+$+29), m/z=234 ($M^+$+41)].

Example 20

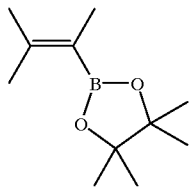

Bis(pinacolato)diboron (0.283 g; 1.11 mmol), 24.1 mg $PdCl_2$(dppf).$CH_2Cl_2$ and 0.416 g (3 mmol) $K_2CO_3$ were placed in a reaction tube under nitrogen. After addition of 0.152 g (1.02 mmol) 2-bromo-3-methyl-2-butene and 5 ml dry DMF the reaction solution was stirred at 30° C. The gc of the reaction solution, after washing an aliquot dissolved in ether with water, had one major peak (over 85% of the integrated area of the gc peaks) identified as the product boronic acid ester by gc/ms. Some (less than 10% of the integrated peak area) of the pinacol ester of diboronic acid remained unreacted. Dimer formation was minimal (less than 2% of the total peak areas).

Example 21

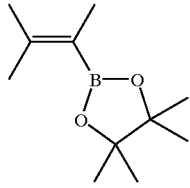

Bis(pinacolato)diboron (0.283 g; 1.11 mmol), 25 mg $PdCl_2$(dppf).$CH_2Cl_2$ and 0.250 g (3 mmol) $NaHCO_3$ were placed in a reaction tube under nitrogen. After addition of 0.146 g (0.98 mmol) 2-bromo3-methyl-2-butene and 5 ml dry ethanol the reaction solution was stirred at 30° C. The gc of the reaction solution, after washing an aliquot dissolved in ether with water, indicated that the product boronic acid ester had formed and this was confirmed by gc/ms. No dimer was observed.

Example 22

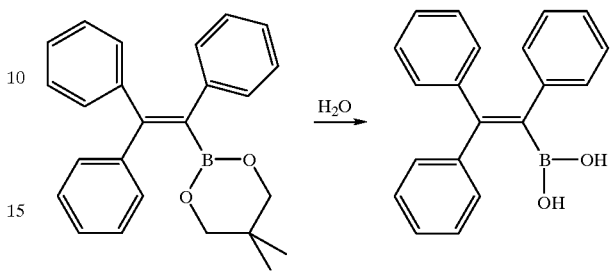

A methanolic solution of gc pure 5,5-dimethyl-2-(1,2,2-triphenylvinyl)-1,3,2-dioxaborinane was analysed by HPLC (Waters 600E) using a Zorbax column (ODS) under the following conditions: λ=230 nm, 2 ml/min., 80% $CH_3CN$: 20% $H_2O$. Two peaks were detected, at 1.9 min. (due to partial hydrolysis) and 7.9 min. (due to the alkene borate). The area ratio starting material/product=5.2.

Some water was added to this sample and the solution allowed to stand at room temperature. After 20 min. HPLC analysis showed a single peak at 1.9 minutes. Analysis of the hydrolysed sample by gc and gc/ms indicated [M-B(OH)$_2$]$^+$. HPLC of triphenylethylene under the same conditions produced a single peak at 8.6 minutes.

The results above indicate rapid hydrolysis of 5,5-dimethyl-2-(1,2,2-triphenylvinyl)-1,3,2-dioxaborinane to 1,2,2-triphenylvinylboronic acid on exposure to water.

Example 23

2,3,4,5-tetramethyl-2,4-hexadiene

This example describes the formation of an alkenylboronic acid ester using a strong base and the subsequent coupling of this boronic acid ester with more alkenyl bromide by raising the reaction temperature to yield the symmetric diene. This reaction proceeds via the alkene borate intermediate.

This intermediate is reacted with 2-bromo-3-methyl-2-butene in the one pot to give

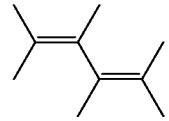

Bis(pinacolato)diboron (0.282 g; 1.11 mmol), 26.4 mg $PdCl_2$(dppf).$CH_2Cl_2$ and $K_2CO_3$(0.0424 g; 3.07 mmol) were placed in a reaction tube under nitrogen. After addition of 2-bromo-3-methyl-2-butene (0.286 g; 1.92 mmol) and 5 ml dry ethanol the reaction solution was stirred at 30° C. for 18 h. The gc of the reaction solution, after washing an aliquot dissolved in ether with water, showed two major peaks identified as the desired alkene borate and the excess 2-bromo-3-methyl-2-butene by gc/ms. A little (less than 2% of the integrated peak area) bis(pinacolato)diboron remained unreacted. No dimer was observed.

The reaction temperature was raised to 60° C. for 23 h and the gc indicated that the alkenylboronic acid ester had all reacted and 2,3,4,5-tetramethyl-2,4-hexadiene was the only major product observed in the gc. This was confirmed by gc/ms.

The formation of the alkenylboronic acid pinacol ester from 2-bromo-3-methyl-2-butene using PdCl$_2$(dppf).CH$_2$Cl$_2$ as catalyst and K$_2$CO$_3$ as base can be carried out at lower temperatures. In DMSO this reaction is slower than in ethanol and this is also the case when potassium acetate instead of K$_2$CO$_3$ is used as base.

High yields of the alkeneboronate are formed with K$_3$PO$_4$ as base and a reaction temperature of 20° C. The alkeneboronate is also formed in dioxane as solvent with little dimer formation when using CsF as base and a reaction temperature of 60° C.

Example 24

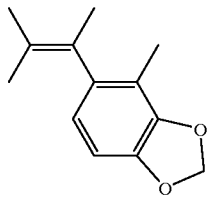

One pot synthesis of this compound proceeded by the initial synthesis of the alkenylboronic acid ester at 30° C. in the presence of K$_2$CO$_3$ and excess bis(pinacolato)diboron followed by the destruction of excess diboron species by base hydrolysis and then addition of 4-bromo-1,2-(methylenedioxy)benzene and raising the reaction temperature to 60° C.

Bis(pinacolato)diboron (0.384 g; 1.51 mmol), 24.7 mg PdCl$_2$(dppf).CH$_2$Cl$_2$ and 0.564 g (4.1 mmol) K$_2$CO$_3$ were placed in a reaction tube under nitrogen. After addition of 0.150 g (1.0 mmol) 2-bromo-3-methyl-2-butene and 5 ml dry ethanol the reaction solution was stirred at 30° C. for 21 h. Following the addition of 0.5 ml of water the reaction was warmed to 30° C. for a further 3 h. The gc of the reaction solution, after washing an aliquot dissolved in ether with water, indicated that the diboron compound was nearly all hydrolysed by the aqueous base.

4-Bromo-1,2-(methylenedioxy)benzene (0.195 g; 0.97 mmol) was then added and the reaction solution warmed to 60° C. for 6 h. All the alkeneborate had reacted and the major product, identified by gc/ms, was the coupled alkenylaryl species. A little biaryl compound was observed in this reaction but this can be reduced further by extending the base hydrolysis time to ensure complete removal of the diboronic acid ester.

Example 25

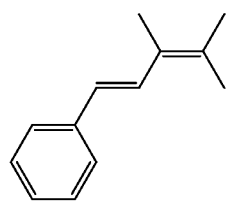

Bis(pinacolato)diboron (0.281 g; 1.10 mmol), 21.1 mg palladium acetate and K$_2$CO$_3$ (0.417 g; 3 mmol) were placed in a reaction tube under nitrogen. After addition of 2-bromo-3-methyl-2-butene (0.149 g; 1.0 mmol) and dry ethanol (5 ml) the reaction solution was stirred at 30° C. for 19.5 h. The gc of the reaction solution had only one major peak (80% of the integrated area) identified by retention time as the desired alkene borate. No 2-bromo-3-methyl-2-butene or bis(pinacolato)diboron were observed in the reaction solution.

The alkenylboronic acid pinacol ester formed was coupled with β-bromostyrene in the presence of palladium acetate by warning the reaction solution to 60° C. without addition of more base. The coupled product was identified by gc/ms.

Example 26

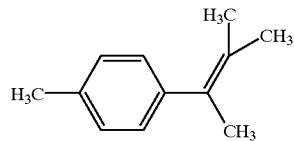

The pinacol ester of diboronic acid (320 mg, 1.2 mmol), 2-bromo-3-methyl-2-butene (149 mg, 1 mmol), PdCl$_2$(dppf).CH$_2$Cl$_2$ (40 mg) and KOAc (300 mg, 3 mmol) were stirred in methanol (6 ml) at 60° C. until all the bromide had reacted (gc analysis of a small sample, new peak at 4.9 min, diboronic ester at 8.1 min). The excess diboron compound was decomposed with H$_2$O (0.5 ml) and Cs$_2$CO$_3$ (960 mg, 3 mmol) by stirring at room temperature for ca. 3 h. p-Iodotoluene (218 mg, 1 mmol) was added and the reaction mixture warned to 60° C. until all the akenylborate had reacted (new peak at 5.4 min in the gc trace).

Example 27

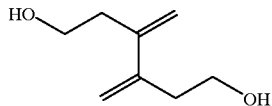

In a Schlenk tube under nitrogen, a mixture of bis(pinacolato)diboron (271 mg; 1.07 mmol), 3-bromo-3-buten-1-ol (146 mg; 0.967 mmol), PdCl$_2$(dppf).CH$_2$Cl$_2$ (26 mg; 0.032 mmol) and potassium carbonate (415 mg; 3.00 mmol) in dry MeOH (5 ml) was sealed and stirred at 30° C. for 18 h. A sample of the reaction mixture was extracted into dichloromethane, washed with dilute HCl$_{(aq)}$ and dried (MgSO$_4$). Analysis of the reaction mixture by gc/ms showed the presence of the dimer (m/z=143; M$^+$+1).

Example 28

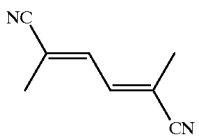

In a Schlenk tube under nitrogen, a mixture of bis (pinacolato)diboron (250 mg; 0.984 mmol), 3-bromo-2-methylacrylonitrile (131 mg; 0.897 mmol), PdCl$_2$(dppf).CH$_2$Cl$_2$ (46 mg; 0.056 mmol) and cesium fluoride (408 mg; 2.69 mmol) in dry dioxane (5.5 ml) was sealed and stirred at 30° C. for 22 h. The gc of the reaction solution showed two major peaks identified as the alkene dimer and unreacted diboron compound by gc/ms. A small amount of the alkene borate was also detected.

Other compounds may be prepared in a similar fashion.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A compound selected from the group consisting of 2-(1,2-dimethylprop-1-enyl)-4,4,5,5-tetramethyl-1,3,2-dioxaborolane, 2-(1,2-dimethylprop-1-enyl)-5,5-dimethyl-1,3,2-dioxaborinane, 5,5-dimethyl-2-(1,2,2-triphenylvinyl)-1,3,2-dioxaborinane, 4,4,5,5-tetramethyl-2-(1,2,2-triphenylvinyl)-1,3,2-dioxaborolane, ethyl (Z)-2(4,4,5,5-tetramethyl-1,3,2-dioxaborolan-2-yl)ethenyl ether, 4,4-dimethyl-2-(4,4,5,5-tetramethyl-1,3,2-dioxaborolan-2-yl)cyclo-hex-2-en-1-one, (E)-2-methyl-3-(4,4,5,5-tetramethyl-1,3,2-dioxaborolan-2-yl)prop-2-enenitrile, ethyl (Z)-3-(4,4,5,5-tetramethyl-1,3,2-dioxaborolan-2-yl)prop-2-enoate, 2-bicyclo[3.2.1]oct-2-en-3yl-4,4,5,5-tetramethyl-1,3,2-dioxaborolane, and 1,2,2-triphenylvinylboronic acid.

2. A compound according to claim 1 which is 2-(1,2-dimethylprop-1-enyl)-4,4,5,5-tetramethyl-1,3,2-dioxaborolane.

3. A compound according to claim 1 which is 2-(1,2-dimethylprop-1-enyl)-5,5-dimethyl-1,3,2-dioxaborinane.

4. A compound according to claim 1 which is 5,5-dimethyl-2-(1,2,2-triphenylvinyl)-1,3,2-dioxaborinane.

5. A compound according to claim 1 which is 4,4,5,5-tetramethyl-2-(1,2,2-triphenylvinyl)-1,3,2-dioxaborolane.

6. A compound according to claim 1 which is ethyl (Z)-2(4,4,5,5-tetramethyl-1,3,2-dioxaborolan-2-yl)ethenyl ether.

7. A compound according to claim 1 which is 4,4-dimethyl-2-(4,4,5,5-tetramethyl-1,3,2dioxaborolan-2-yl)cyclo-hex-2-en-1-one.

8. A compound according to claim 1 which is (E)-2-methyl-3-(4,4,5,5-tetramethyl-1,3,2-dioxaborolan-2-yl)prop-2-enenitrile.

9. A compound according to claim 1 which is ethyl (Z)-3-(4,4,5,5-tetramethyl-1,3,2-dioxaborolan-2-yl)prop-2-enoate.

10. A compound according to claim 1 which is 2-bicyclo[3.2.1]oct-2-en-3yl-4,4,5,5-tetramethyl-1,3,2-dioxaborolane.

11. A compound according to claim 1 which is 1,2,2-triphenylvinylboronic acid.

* * * * *